US 8,216,180 B2

(12) United States Patent
Tschirren et al.

(10) Patent No.: US 8,216,180 B2
(45) Date of Patent: Jul. 10, 2012

(54) ADMINISTERING APPARATUS WITH FUNCTIONAL DRIVE ELEMENT

(75) Inventors: Markus Tschirren, Kirchberg (CH); Ulrich Moser, Heimiswil (CH); Juerg Hirschel, Aarau (CH); Jan Baumert, Bern (CH); Eric Hattler, Solothurn (CH)

(73) Assignee: TecPharma Licensing AG, Burgdorf (CH)

( * ) Notice: Subject to any disclaimer, the term of this patent is extended or adjusted under 35 U.S.C. 154(b) by 60 days.

(21) Appl. No.: 12/572,759

(22) Filed: Oct. 2, 2009

(65) Prior Publication Data
US 2010/0087785 A1 Apr. 8, 2010

Related U.S. Application Data
(63) Continuation of application No. PCT/CH2007/000560, filed on Nov. 12, 2007.

(30) Foreign Application Priority Data
Apr. 5, 2007 (DE) .......................... 10 2007 016 810

(51) Int. Cl.
*A61M 37/00* (2006.01)
(52) U.S. Cl. ........................................................ 604/82
(58) Field of Classification Search .................. 604/82, 604/85, 89–91, 209
See application file for complete search history.

(56) References Cited

U.S. PATENT DOCUMENTS
4,968,299 A * 11/1990 Ahlstrand et al. .............. 604/90
6,793,646 B1 * 9/2004 Giambattista et al. .......... 604/90

FOREIGN PATENT DOCUMENTS
| DE | 10 2004 055298 A1 | 5/2006 |
|---|---|---|
| EP | 0 298 067 B1 | 10/1991 |
| EP | 0 793 973 A2 | 9/1997 |
| EP | 1 066 847 A | 1/2001 |
| EP | 0 911 046 B1 | 12/2004 |

* cited by examiner

*Primary Examiner* — Kevin C Sirmons
*Assistant Examiner* — Bradley Osinski
(74) *Attorney, Agent, or Firm* — Dorsey & Whitney LLP; David E. Bruhn, Esq.

(57) ABSTRACT

An apparatus for administering a fluid product, including a housing, a product member for accommodating the fluid product and/or a reservoir for the fluid product, which product member can be moved relative to the housing from a start position to an inserted position along a longitudinal axis of the housing, a drive member in the housing and movable relative to the product member for emptying the fluid product from the product member and/or the reservoir, wherein the drive member has at least one holding element which holds the drive member in the start position of the product member and wherein, by the movement of the product member, the holding element is moved from the holding position to a released position in which the drive member is movable relative to the housing.

3 Claims, 6 Drawing Sheets

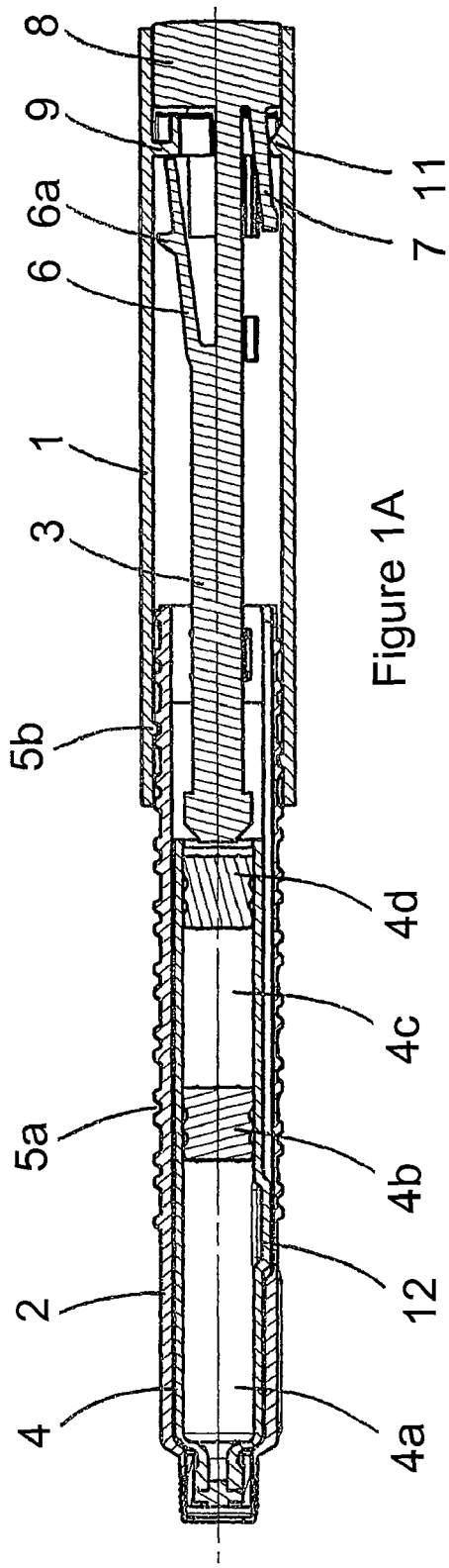
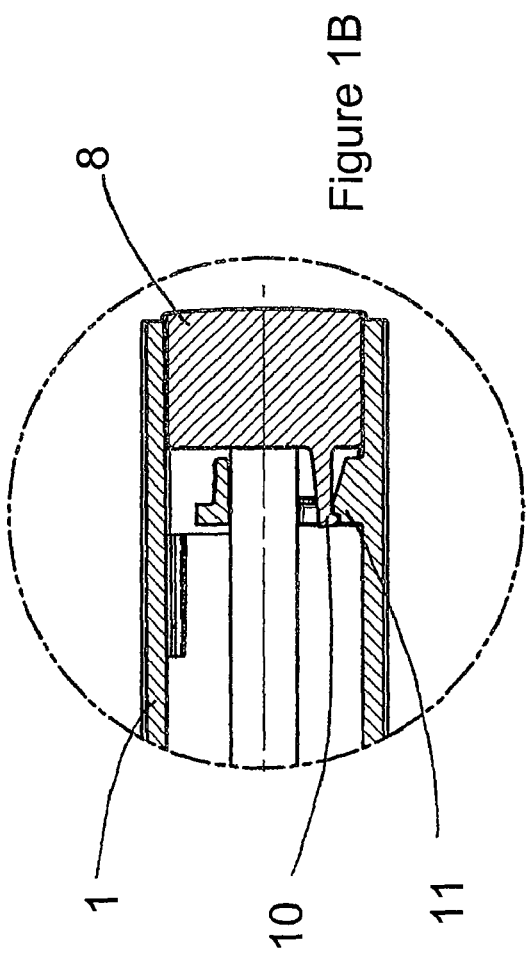

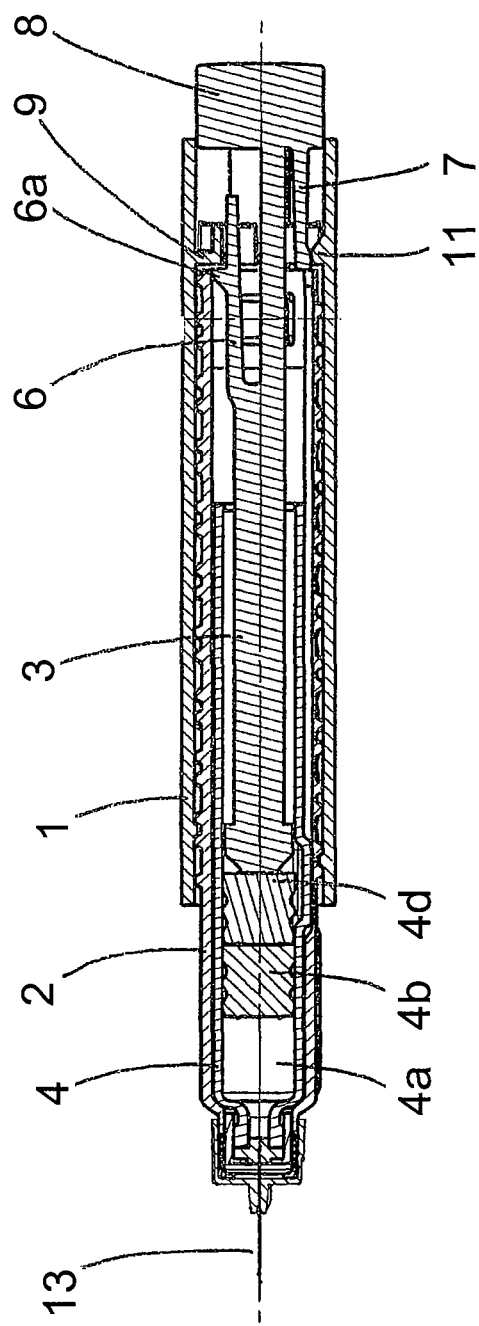
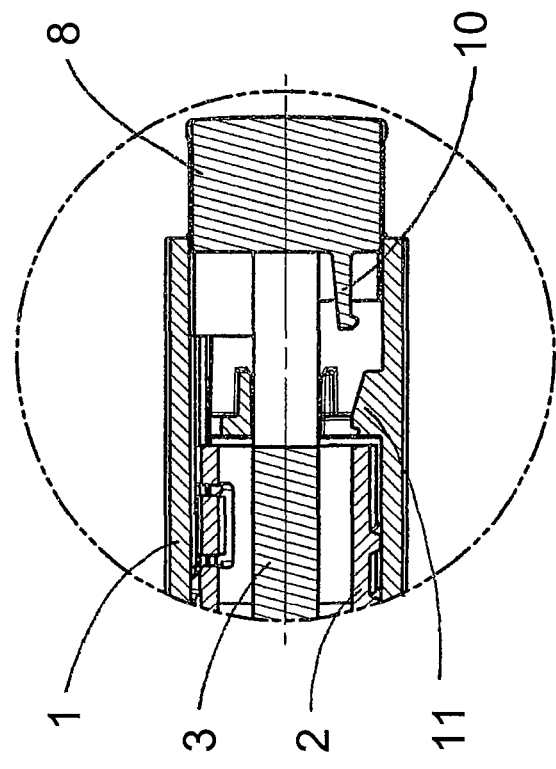
Figure 4A
Figure 4B

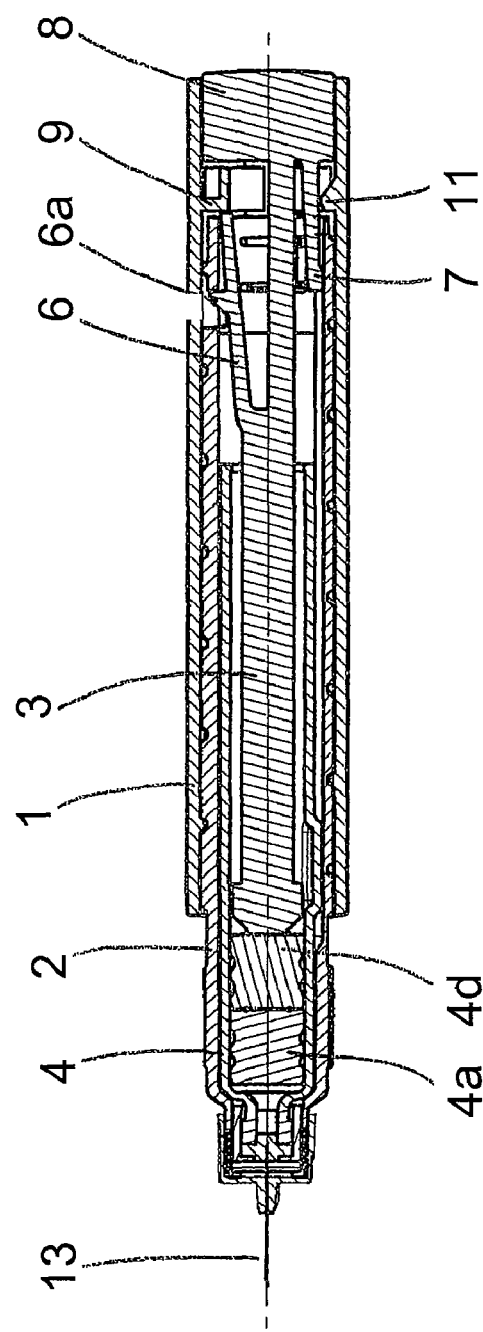
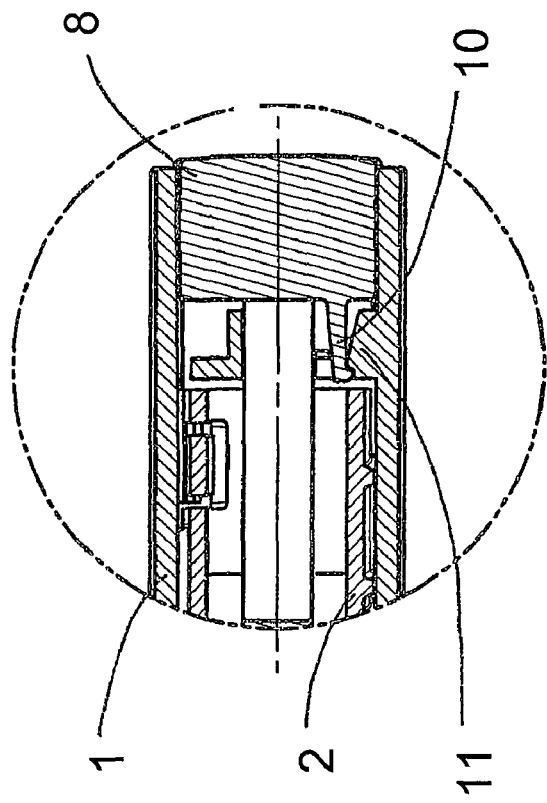
Figure 5A
Figure 5B

ADMINISTERING APPARATUS WITH FUNCTIONAL DRIVE ELEMENT

CROSS-REFERENCED RELATED APPLICATIONS

This application is a continuation of International Patent Application No. PCT/CH2007/000560 filed Nov. 12, 2007, which claims priority to German Patent Application No. DE 10 2007 016 810.3 filed Apr. 5, 2007, the entire contents of both of which are incorporated herein by reference.

BACKGROUND

The present invention relates to devices for injecting, administering, infusing, dispensing or delivering a substance, and to methods of making and using such devices. More particularly, it relates to a device for administering a fluid or liquid product or substance such as a medicinal or therapeutic substance, and to a method for preparing the device for performing an administration. More particularly, in some embodiments, the present invention relates to a device for administering an active agent from a two-chamber reservoir, wherein the device comprises a controller and/or a control means for controlling the progression for preparing and administering the fluid product.

A multitude of administering devices are known from the prior art, using which a liquid or fluid drug or other fluid product can be administered from a container such as a glass carpoule or ampoule. The product container is inserted into the administering device, wherein a drive member or drive element such as a piston rod is connected to a stopper in the container to move the stopper to administer the product. A movement of the drive member relative to the container of the administering device advances the stopper within the container, such that the drug is delivered through an injection needle connected to the container. The use of such administering apparatus is facilitated by the fact that the devices are intended to be used once, i.e. once a container has been emptied, the administering device together with the container is disposed of. Changing the container is not necessary. It is also common for the length of the advancing movement for delivering the drug to be predetermined by structural measures and to not have to be set by the user. In addition, devices are also known in which a separate venting or priming step is provided, by which a quantity of air which may be situated in the container is removed from the container before the active agent is delivered. Lastly, there are administering devices which are specialized for administering fluid products from two-chamber carpoules or containers. In such two-chamber carpoules, it is necessary to mix the fluid product to be administered shortly before use, since the active agent is, for example, provided in a solid form in a first chamber and a corresponding solvent for the active agent is provided in a second chamber. To mix the fluid product, a fluid connection between the two chambers is established by advancing the stoppers within the carpoule, such that the solvent enters the chamber of the solid active agent. The use of such a two-chamber carpoule and how it is mixed is known from, for example, EP 0 298 067 B1.

A pre-filled syringe is known from EP 0 911 046 B1. The syringe comprises a piston rod comprising a stopping means for mixing a product in a two-chamber container, wherein the progression when mixing the product is controlled by the stopping means. For this purpose, the stopping means projects laterally from the piston rod, such that it abuts against the rim of the container when the piston rod is slid in and stops the movement of the piston rod. The solvent then enters the chamber of the active agent via a bypass, such that the product is mixed. Sliding the piston rod further in folds the stopping means towards the axis of the piston rod and inserts it into a cavity within the piston rod, such that the piston rod can be slid further into the container. Continuing to slide the piston rod in enables the product to be delivered from the container.

A similar device is known from EP 0 793 973 A2. In this double-chamber syringe, the circumference of the piston rod comprises one or more protrusions which briefly interrupt the advancing movement of the piston rod into the syringe container. The interruption serves as an indication that the solvent has entered the active agent chamber via the bypass and the mixing procedure has been completed. Sliding the piston rod further in overcomes the resistance from the protrusions and enables the product to be delivered from the syringe. (The disclosures and teachings of the three EP documents cited herein above are incorporated herein by reference.)

SUMMARY

Objects of the present invention include to provide a device for administering a fluid product which simplifies and co-ordinates the progression for preparing the device and the administering procedure, minimizes the chance of erroneous use of the device, and comprises a reduced number of components and is cost-effective to manufacture. It is another object of the present invention to make administering a fluid product from a two-chamber reservoir easier and more secure. It is another object of the present invention to provide a method for preparing an administering device which simplifies the handling of the device and minimizes the chance of error.

In one embodiment, the present invention comprises an apparatus for administering a fluid product, comprising a housing, a product member for accommodating the fluid product, which product member can be moved relative to the housing from a start position to an inserted position along a longitudinal axis of the housing, a drive member in the housing and movable relative to the product member for emptying the fluid product from the product member, wherein the drive member comprises a holding element having a holding position and a released position, wherein the holding element holds the drive member in the start position of the product member and wherein, by the movement of the product member, the holding element is moved from the holding position to the released position in which the drive member is movable relative to the housing.

In one embodiment, the present invention comprises an apparatus for administering a fluid product, comprising a housing, an intake or accommodating member for the fluid product and/or for a reservoir for the fluid product, which intake or accommodating member can be introduced from a start position into an inserted position along a longitudinal axis of the housing relative to the housing, a drive member which lies in the housing and which is movable relative to the intake or accommodating member for emptying the fluid product out of the intake or accommodating member and/or the reservoir, wherein the drive member has at least one holding element which holds the drive member in the start position of the intake or accommodating member relative to the housing and, by the insertion of the intake or accommodating member, the holding element is moved from the holding position into a released position in which the drive member is movable relative to the housing.

In some embodiments, a device for administering a fluid product in accordance with the present invention comprises a housing into which an accommodating member for containing the fluid product and/or a reservoir containing the fluid product can be inserted. (The accommodating member may be thought of and/or referred to as an intake member.) A drive member is mounted in the housing and is moved relative to the accommodating member to deliver the fluid product. The housing is formed in the shape of a cavity and can be formed from one or more elements. The accommodating member for the fluid product is, for example, formed as a holder for a product reservoir such as a two-chamber carpoule or ampoule. In some preferred embodiments, the accommodating member encloses the product reservoir and provides a receptacle in its distal region for attaching an injection needle which establishes a fluid connection to the interior of the product reservoir. At its proximal end, the accommodating member is connected to or inserted into the housing. The accommodating member can be moved relative to the housing along a longitudinal axis of the housing from an initial position to an inserted position and/or inserting position, wherein the accommodating member can be completely or partially inserted into the interior of the housing. A guide or guiding means is provided for inserting the accommodating member into the housing and guiding the movement of the accommodating member with respect to the housing. For example, grooves or flutes can be provided on the housing or the accommodating member, and corresponding protrusions or cams which run or travel within the grooves can be provided on the other element. In some preferred embodiments, the guiding means is a threaded guide. To this end, an inner thread is provided on the inner area of the housing, and an outer thread is provided on the outer side of the accommodating member and is guided in the inner thread of the housing.

Accordingly, in some embodiments, the insertion movement for inserting the accommodating member into the housing is performed along the longitudinal axis of the housing in the proximal direction by a helical movement between the housing and the accommodating member. The speed of the translational movement of the parts with respect to each other can be set or selected via selecting the pitch of the thread.

In some embodiments, the drive member mounted in the housing serves to deliver the fluid product from the product reservoir, i.e. serves to advance a stopper within the reservoir in the distal (front, forward or delivery) direction. To this end, the drive member can be moved relative to the housing in the distal direction. The drive member may be formed by a piston rod. If the administering device is situated in a position in which it is ready to administer a product, the piston rod protrudes out of the housing at the proximal end, such that an advancing movement for the stopper within the reservoir can be generated by sliding the piston rod in, in the distal direction of the housing, wherein the piston rod can be slid in manually. It is also possible to provide an automatic delivery, for example by a force element such as a spring which exerts a force on the drive member to advance it.

In accordance with some embodiments of the present invention, the drive member comprises a control or control means using which the progression when handling the administering device can be controlled, i.e. the sequential order of mixing, venting, dosing-up, injecting and blocking or locking the device. In some embodiments, the control means is formed by a functional drive member which mechanically controls the sequence of the individual steps. To this end, the drive member features at least one holding element. The holding element holds the drive member relative to the housing in the initial position between the accommodating member and the housing. In the holding position, the drive member cannot therefore be moved relative to the housing in a proximal (rearward) direction along the longitudinal axis of the housing. In the holding position, the drive member is also mounted in the housing such that a movement relative to the housing in the distal direction is also prevented. To this end, an abutment can be provided on the drive member and a counter abutment can be provided on the housing or on a part which is fixed with respect to the housing, which prevent a movement of the drive member in the housing in the distal direction. In the holding position, the drive member is therefore obstructed both from moving in the distal direction with respect to the housing and from moving in the proximal direction with respect to the housing, i.e. an effective connection exists, such that the holding element is fixed, i.e. cannot be moved, relative to the housing.

In accordance with some embodiments of the present invention, the drive member is released relative to the housing by inserting the accommodating member. The relative movement between the accommodating member and the housing thus releases the effective connection between the drive member and the housing and/or an element of the device which is fixed with respect to the housing. In this released position and/or releasing position, the drive member can be moved relative to the housing in the proximal direction. It is therefore possible to move the drive member relative to the housing into a position which can be referred to as a dosing-up position and from which a delivery stroke can be performed relative to the housing in the distal direction.

In some embodiments, the holding element is coupled to the housing to hold the drive member. This can be achieved by direct contact between the holding element and the housing, or also mediated by intermediate elements within the administering device which are fixed with respect to the housing. To release the drive member from the holding position, the drive member is decoupled from the housing or from a part which is fixed with respect to the housing. The holding position is, for example, realized by the holding element abutting against an axial abutment which is fixed with respect to the housing and prevents an axial movement along the longitudinal axis of the housing, the holding element and thus the drive element.

In a preferred embodiment, the holding element of the drive member is formed as at least one flexible continuation which projects radially from the drive member. The flexible continuation is formed as an arm or brace which can be an integral component of the holding element or can be molded on it. Accordingly, the holding element projects radially from the drive member but can be moved relative to the drive member due to its flexibility. The holding element does, however, exhibit enough rigidity that a tensing force is required to deflect it out of its base position relative to the drive member. The flexible continuation is therefore spring-elastically arranged on the holding element. By applying a force, it is possible to move the holding element and/or continuation with respect to the drive member, e.g. radially toward the axis of the drive member. In a preferred embodiment, the flexible continuation projects from the holding element substantially in the direction of the insertion movement of the accommodating member. This can, for example, be provided by a small arm which is splayed or split in the shape of a fork and fixed on the drive member at its proximal end and projects from the drive member with its proximal end. In the holding position, the proximal end of the small arm abuts against an abutment which is fixed with respect to the housing or against an edge and thus prevents a movement of the drive member in the proximal direction.

In some embodiments, to release the holding position and/or the holding engagement or the effective connection, the accommodating member engages with the holding element as it is being inserted and moves the holding element into the releasing position. If the holding element is formed as a flexible continuation in the form of a small arm which is splayed away from the drive member, the accommodating member can, for example, be slid over the small arm during the insertion movement into the housing and thus exert a force on the small arm which acts radially inwardly. The holding element is thus moved out of its holding position and the drive member is therefore released for a movement in the proximal direction.

In one embodiment, a device for administering a fluid product in accordance with the present invention comprises a product reservoir in the form of a two-chamber reservoir. The two-chamber reservoir comprises a first chamber for an active agent, which is limited by a first stopper, and a second chamber for a solvent, which is limited by the first stopper and a second stopper, as is known from the prior art. The chambers can be connected via a bypass in the wall of the reservoir by shifting the stoppers, to enable the active agent and the solvent to be mixed. In accordance with the present invention, the holding element is formed in the holding position such that the drive member abuts against the second stopper when the accommodating member is inserted and shifts the second stopper relative to the accommodating member during insertion, until the accommodating member is in a mixing position in which the active agent can be mixed with the solvent. In some preferred embodiments, subsequent to mixing, the product reservoir is vented to eliminate air remaining in the reservoir from the reservoir, before the product is administered. Such a venting procedure may, of course, be necessary and/or performed in one-chamber reservoirs. To this end, the accommodating member is inserted further into the housing in the proximal direction, from the mixing position—or, in the case of a one-chamber reservoir, the initial position—to a venting position, wherein the stopper within the reservoir is shifted further in the distal direction. For venting, in some embodiments it is necessary to attach a needle unit to the accommodating member, wherein said needle unit establishes a connection between the reservoir and the environment, such that the air can escape from the reservoir via the needle when the stopper is shifted.

In accordance with some embodiments of the present invention, the drive member remains in the holding position with respect to the housing until the mixing procedure in the two-chamber reservoir and/or also the venting procedure have been completed. The mixing and venting procedure is performed by rotating the accommodating member along the threaded guide within the housing. In some preferred embodiments, at the time of the mixing or venting procedure, i.e. as soon as the accommodating member has been screwed far enough into the housing, the holding position of the drive member is released simultaneously by removing the block on the drive member by the holding element on the housing or the part which is fixed with respect to the housing. The accommodating member is then situated in an inserted position in which it need not or cannot be screwed further into the housing. To release the holding position, it is also possible to insert the accommodating member slightly further into the housing, beyond the mixing or venting position, until the released position has been reached.

In one embodiment of the present invention, in the holding position the drive member is mounted within the housing such that the proximal end of the drive member, which can be formed as a drive button, comes to rest within the housing. The drive member is therefore protected against intervention by the user in the position of the administering device before the accommodating member and/or a two-chamber reservoir is inserted and, in some preferred embodiments, also before a venting procedure or mixing procedure. It is not possible to operate the administering apparatus to deliver the fluid product. In some preferred embodiments, the drive button on the drive member ends flush with the proximal end of the housing. The drive member and/or the drive button can remain in this initial position while the accommodating member is inserted for venting or mixing the reservoir. It can however be extended out of the housing even during the insertion movement for venting or mixing, by this movement.

In accordance with one preferred embodiment of the present invention, the drive member features an activating element or activating member with which the accommodating member engages during the insertion movement and which moves the drive member relative to the housing into an activated position. This activated position is defined by the drive member extending out of the proximal (rear) end of the housing. It would, however, also be possible for the drive member to comprise an operating element which is moved into an activated position by a lateral movement, for example to subsequently trigger a drive spring. To operate the activating element, it can comprise an axial abutment which abuts against the accommodating member during the insertion movement. The activating element can, for example, be formed by a continuation which projects from the drive member in the distal direction. When the accommodating member is inserted into the housing, the activating element can abut against the proximal end of the accommodating member and/or its edge. Continuing the insertion movement transfers the movement onto the drive member via the activating element, and the latter is shifted together with the accommodating member in the proximal direction. The activating element can be formed to be flexible, comparable to the holding element, and can exhibit a bias such that it can be moved counter to the bias, out of its abutting position on the accommodating member. To this end, the activating element can, for example, be radially bent toward the axis of the drive member. To this end, a guiding protrusion can be provided, for example on the housing. In this bent-in position, the activating member yields to the rim of the accommodating member inwardly, such that the drive member can be shifted relative to the accommodating member in the distal direction.

In some embodiments, in the activated position, the drive member can thus be shifted relative to the housing and to the accommodating member in the distal direction, such that it can perform a delivery stroke. The delivery stroke shifts the stopper in the product reservoir and delivers product from the reservoir through an injection needle. In this delivery position or end position, after the fluid product has been administered, the activating element lies within the accommodating member. in some preferred embodiments, the drive button of the drive member and/or the end of the drive member also comes to rest again within the housing.

In some embodiments, in the end position the holding element abuts against the abutment which is fixed with respect to the housing, i.e. the holding element is again situated in its deflected position, as at the beginning before the accommodating member was inserted into the housing. Thus, the holding member again prevents a proximal movement of the drive member with respect to the housing, wherein the holding element then comes to rest substantially within the accommodating member in said end position. In the end position, the administering device is blocked against being operated again. This is achieved by the abutment between the holding element and the housing and the latching of the accommodating member with respect to the housing once the accommodating member has been completely inserted into the housing.

In some embodiments, it is possible to provide a limiting element on the drive member, e.g. on the holding element of the drive member, which limits a movement of the drive member in the proximal direction relative to the housing by abutting against a part which is fixed with respect to the housing. The limiting element may be, for example, formed as a heel on the holding element; during the insertion movement of the accommodating member, the holding element can be deflected out of the holding position, such that the drive member can be slid out or moved in the proximal direction relative to the housing by the activating element. The sliding-out movement is, however, limited by the heel, which abuts against the part which is fixed with respect to the housing as soon as the drive member has been moved out of the housing by an extending stroke. The heel also advantageously serves as a guiding coulisse, e.g., a groove, glide, etc., for the accommodating member when operating the holding element, i.e. when deflecting the holding element out of the holding position into the released position.

In some embodiments, if the drive member is shifted relative to the housing and to the accommodating member in the distal direction to deliver the product, the holding element may be moved or slid into the interior of the accommodating member. In some embodiments, to ensure that the holding element can return to its holding position, a cavity is provided in the accommodating member, with which the heel of the holding element can engage in the end position. This ensures that the holding element is reliably restored to the holding position and that the administering device is blocked against being used any more.

In some embodiments, a method for preparing an administering device in accordance with the present invention comprises the following steps: The accommodating member and/or reservoir is inserted into the housing, from an initial position to a venting position, wherein the accommodating member travels a first insertion distance. While this first insertion distance is being traveled, the drive member is held in the holding position relative to the housing, and a stopper within the reservoir is advanced. In the next step, the drive member is released from the holding position by inserting the accommodating member further into the housing. The holding position is released while the accommodating member is being advanced relative to the housing over a second insertion distance. The drive member is then situated in a released position in which it is no longer held against moving relative to the housing in the proximal (rearward) direction. In a subsequent step, the drive member is extended in the proximal direction relative to the housing by inserting the accommodating member even further. The drive member is extended while the accommodating member moves over a third insertion distance. After this step, i.e. after the third insertion distance has been overcome, the accommodating member is situated in an inserted position and the drive member is situated in an activated position.

In some preferred embodiments, the method for preparing an administering device in accordance with the present invention comprises a step according to which mixing is performed within a two-chamber reservoir while the accommodating member is being inserted, by a stopper being advanced within the two-chamber reservoir by the drive member. In this step, the accommodating member is shifted from the initial position to a mixing position. This mixing procedure can be performed during the first insertion distance of the accommodating member as described above. This mixing distance is then followed by the accommodating member advancing from the mixing position to the venting position. The venting procedure can likewise be performed during the first insertion distance of the accommodating member.

In some embodiments, the method for preparing an administering device in accordance with the present invention represents a progression control for the progression of the individual steps when providing the administering device for a user, wherein the embodiment of the drive member in accordance with the present invention, comprising a holding element and/or also an activating element, serves as a controller or control means for controlling the individual steps. In the case of active agents which have to be stored in a dried state and dissolved in a solvent only shortly before being administered by injection, the individual steps should be performed carefully and exactly when preparing the administering device. With the aid of the method of the present invention, individual preparation steps of mixing, venting, dosing-up, injecting and blocking the device are ordered so that a user should not forget a step, perform a step carelessly or skip a step. Locking or blocking the injection device, e.g. an injection pen, after the product has been administered helps prevent an administering device which has already been used from being inappropriately handled.

In accordance with other aspects of the present invention, a lock or latching means and/or an indicator or indicating means relative to inserting the accommodating member into the housing is provided in a device for administering a fluid product. Thus, in some embodiments, to avoid misuse of the device, after the accommodating member has begun to be inserted into the housing, it is not possible to reverse any of the individual preparation steps after they have been completed. In some embodiments, an indicator indicates when the individual preparation steps have been completed, wherein the indication can, for example, be provided by a visual marking or an acoustically perceptible sound. To this end, a catch or catch means are provided which block or lock the accommodating member against a movement counter to the insertion direction after each preparation step. In some embodiments, it is optionally also possible to form the catch to be releasable, should this seem expedient. In the case of a threaded guide between the housing and the accommodating member, the catch forms, for example, a reverse rotational block against the accommodating member rotating out of the housing again. Such a reverse rotational block can, for example, be realized by a resilient snap arm on the accommodating member or on the housing, which latches into a cavity in the housing and/or accommodating member in the reverse rotational direction but can slide out of the cavity in the forward movement. Such a reverse rotational block may be, for example, provided when the mixing procedure and the venting procedure have been completed. In addition, such a reverse rotational block could be provided even as the accommodating member is being inserted into the housing, i.e. even in the initial position, the accommodating member is already secured against rotating completely out of the housing by a catch. The latching simultaneously forms an indication that the corresponding preparation step has been completed. In the inserted position after mixing and venting, the catch can be formed such that a movement in the proximal direction, i.e. a screwing-in movement, is also blocked. In the inserting position, the accommodating member is accordingly secured both against insertion and/or rotating in and extending and/or rotating out. Alternatively, the accommodating member can be provided by a latching with, for example, the limiting element of the drive member, as described above.

In some embodiments, the catches and/or reverse rotational blocks are advantageously formed such that latching or snapping into the catch simultaneously generates an acoustic signal, such that the completion of the individual preparation steps is made audible. The sequence of the individual preparation steps is therefore acoustically indicated to a user.

BRIEF DESCRIPTION OF THE DRAWINGS

FIG. 1A depicts an embodiment of an administering device in accordance with the present invention, in an initial position.

FIG. 1B is a detailed view of the administering device from FIG. 1A, rotated by 90°.

FIG. 4A depicts an embodiment of an administering device according to the present invention, in an inserted position.

FIG. 4B is a detailed view analogous to FIG. 1B, in the inserted position.

FIG. 5A depicts an embodiment of an administering device according to the present invention, in an end position.

FIG. 5B is a detailed view analogous to FIG. 1B, in the end position.

DETAILED DESCRIPTION

Figure 2:
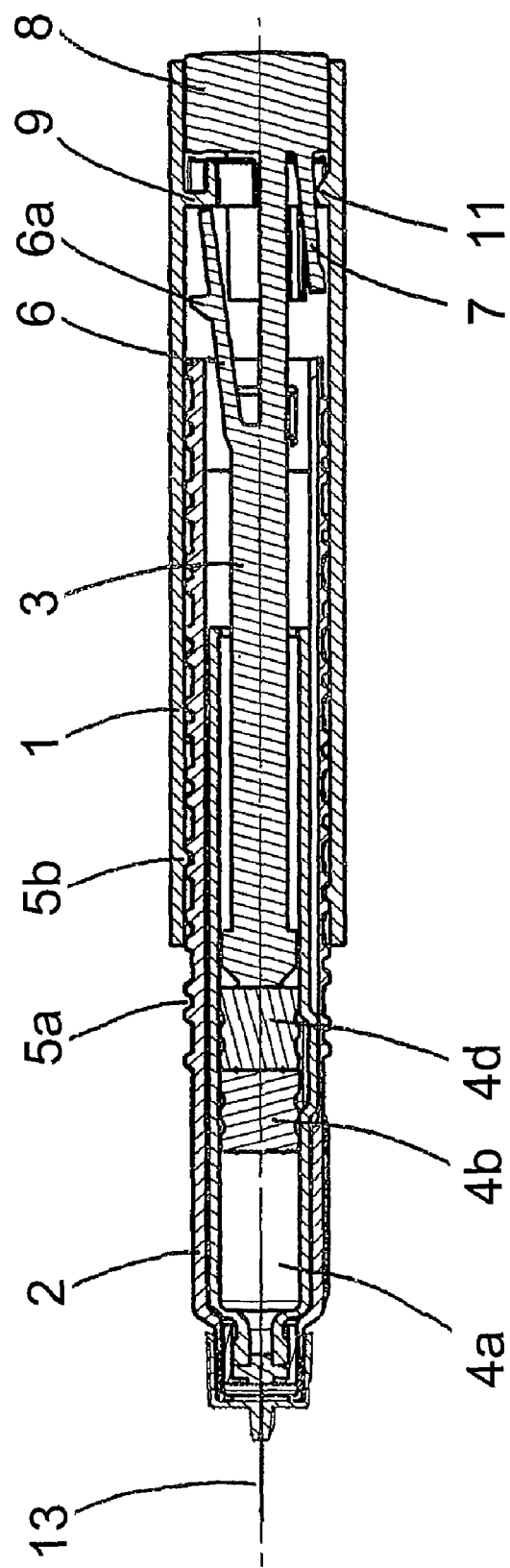
FIG. 2 depicts an embodiment of an administering device according to the present invention, in a mixing position.

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless stated otherwise, positional terms (e.g., up, down, front, rear, distal, proximal, etc.) are descriptive not limiting. Same reference numbers are used to denote same parts or components.

FIG. 1A shows an embodiment of a device for administering a fluid product in accordance with the present invention, in an initial position. The device comprises a housing 1, an accommodating member 2 and a drive member 3. In some embodiments, the device comprises these three components alone. In other embodiments, a product reservoir comprising a desired product to be administered and a matching injection needle is added. It is an advantage of the present invention that an administering device in accordance with the present invention may comprise only a few individual components. This reduces the cost of producing and assembling the components.

In accordance with the exemplary embodiment shown, the product reservoir is a two-chamber reservoir which comprises a first chamber 4a, which is limited by a stopper 4b, and a second chamber 4c which is limited by the first stopper 4b and a second stopper 4d. In addition, a bypass 12 (cf. FIGS. 4a and 5a) is provided in the circumference of the wall of the product reservoir, wherein solvent from the second chamber 4c can be diverted into the product chamber 4a through said bypass 12.

The proximal end of the accommodating member 2 is partially inserted into the distal end of the housing 1. A guide or guiding structure is provided between the housing 1 and the accommodating member 2 and guides a relative movement between the housing 1 and the accommodating member 2. The guiding structure comprises a guiding groove 5a which circulates on the outer circumferential area of the sleeve-shaped accommodating member 2 in the manner of a thread. A complementary guiding cam 5b is provided on the inner circumferential area of the housing 1, which is likewise formed in the shape of a sleeve, and is guided within the guiding groove 5a. The guiding cam 5b can also be formed as a guiding rail or as a guiding segment. In the exemplary embodiment, the guiding structure 5a, 5b is embodied as a threaded guide. A rotational movement of the accommodating member 2 relative to the housing 1 axially inserts the accommodating member 2 into the housing 1 in the proximal direction.

The drive member 3 is formed in the shape of a rod. In the initial state in accordance with FIG. 1A, the distal end of the drive member 3 comes to rest opposite the proximal stopper 4d of the product reservoir 4. The administering apparatus in the initial position in accordance with FIG. 1A corresponds to a sale or dispatched state wherein the device is situated when it is sold or dispatched to a user.

The proximal end of the drive member 3 features a holding element 6 and an activating element 7. In some preferred embodiments, the holding element 6 and the activating element 7 are integral components of the drive member 3. It is, however, also possible to join the holding element 6 and the activating element 7 to the rod-shaped region of the drive member. The proximal end of the drive member 3 also comprises a swelling which can be referred to as a drive button 8. The drive button 8 is inaccessible for a user in the initial position, since it is countersunk in the housing 1.

The holding element 6 and the activating element 7 project laterally from the drive member as flexible continuations or arms. It is in principle possible to provide two or more such arms on the drive member. The holding element 6 projects from the drive member 3 in the proximal (rearward) direction, and the activating element projects from the drive member 3 in the distal (forward) direction.

In the initial position shown in FIG. 1A, the holding element 6 comes to rest in the axial direction opposite a protrusion and/or edge 9 of the housing which protrudes inwardly. Accordingly, the proximal end of the holding element abuts against the housing protrusion 9 in the axial direction. In this position, the holding element is in its base position. The holding element can, however, be flexibly biased such that it can be moved in the radial direction toward the axis of the drive member 3. The activating member 7 projects from the drive member 3 obliquely in the distal direction. The activating element is in a relaxed state in the initial position, but can be flexibly deflected in the radial direction toward the axis of the drive member. When preparing the administering device, they fulfil functions for the progression control of the individual preparation steps. In some embodiments, together with the drive member, they comprise the control means for the progression control.

FIG. 1B shows a detailed view of the proximal region of the administering device in accordance with FIG. 1A, in which the device is rotated by 90°. A securing element 10 can be seen which co-operates with a protrusion 11 on the housing 1. The securing element 10 and the protrusion 11 together form a clamping connection to secure the drive member 3, in addition to the block, by the abutment between the holding element 6 and the housing protrusion 9 and by the abutment between the drive button 8 and the housing protrusion 9.

The abutment between the holding element 6 and the housing protrusion 9 in the axial direction causes the movement of the drive member in the proximal direction relative to the housing to be blocked or prevented. Conversely, the abutment between the drive button 8 and the housing protrusion 9 prevents the drive member 3 from being moved in the distal direction relative to the housing.

FIG. 2 shows an administering device in accordance with the present invention in a mixing position. An injection needle 13 has been attached to the distal end of the device. From the initial position in accordance with FIG. 1A, the accommodating member 2 is inserted and/or screwed into the interior of the housing along the guiding structure 5a, 5b relative to the housing 1 in the proximal direction, wherein the drive member 3 remains fixed relative to the housing due to the block between the holding member 6 and the housing protrusion 9 and also due to the block between the securing element 10 and the protrusion 11. By inserting the accommodating member 2, the distal end of the drive member 3 hits the stopper 4d of the product reservoir 4 and slides it in the distal direction within the product reservoir when the insertion movement is continued. This initially transfers the drive force onto the stopper 4b through the solvent in the chamber 4c, such that both stoppers 4b and 4d are driven distally. As soon as the stopper 4b comes to rest in the region of the bypass, the stopper 4b remains at rest relative to the reservoir 4. The stopper 4d, by contrast, continues to be driven, such that the solvent from the chamber 4c enters the chamber 4a via the bypass and can dissolve an active agent situated in the chamber 4a. The stopper 4d is driven until it hits the stopper 4b. The mixing position of the administering apparatus is thus reached. During this procedure, the accommodating member 2 is continuously inserted further into the housing 1. The drive member 3, however, remains at rest.

Figure 3:
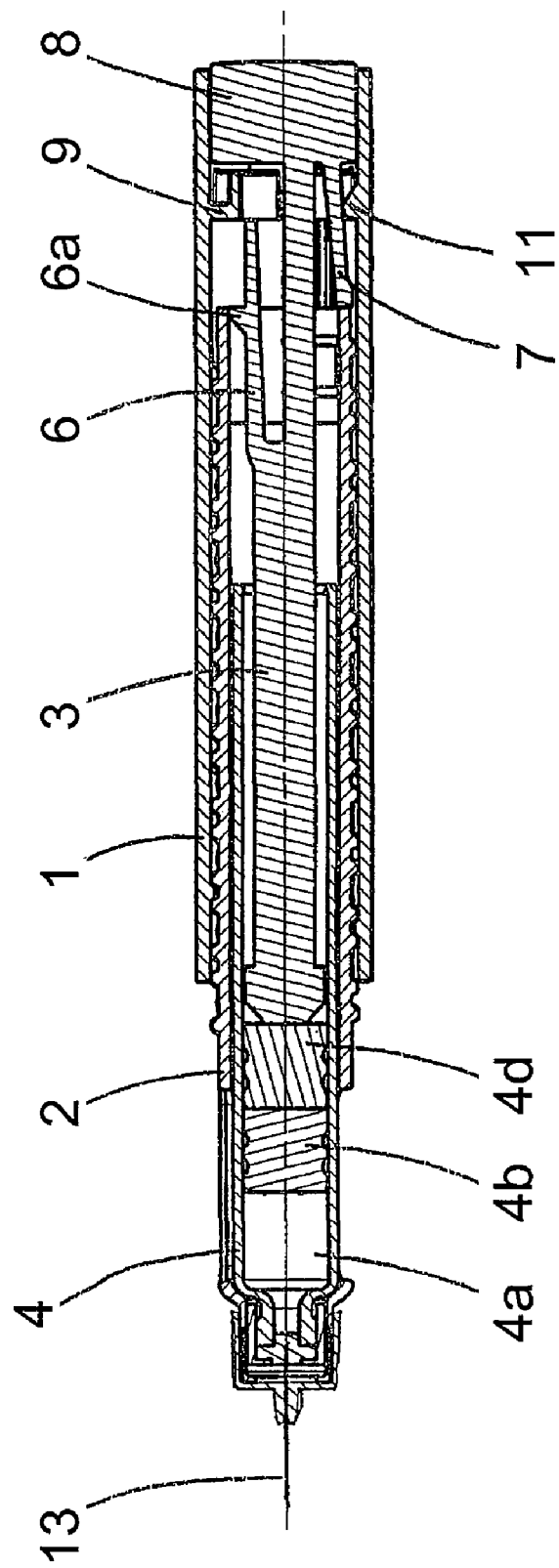
FIG. 3 depicts an embodiment of an administering device according to the present invention, in a venting position.

FIG. 3 shows an administering device in accordance with the present invention in a venting position. From the mixing position shown in FIG. 2, the accommodating member 2 is inserted further into the housing 1 in the proximal direction. Up to this point, the accommodating member 2 has been inserted into the housing over a first insertion distance, wherein the holding element 6 remains in the holding position. The proximal rim of the accommodating member 2 then abuts against a heel 6a on the holding member 6. The heel 6a comprises an oblique plane which is aligned opposite the proximal end of the accommodating member. If the accommodating member 2 is inserted further into the housing over a second insertion distance, the proximal end abuts against the oblique area of the heel 6a and slides off on said area, wherein the holding element 6 is deflected in the radial direction toward the axis of the drive member 3. The holding element 6, in the form of a functional arm, is deflected out of abutment with the housing protrusion 9. From the mixing position to said released position, in which the holding element 6 of the drive member 3 is deflected out of its holding position for holding the drive member 3 relative to the housing 1, the accommodating member 2 travels a second insertion distance which can also be referred to as the releasing distance. As soon as the holding element 6 is deflected out of abutment with the housing protrusion 9, the proximal end of the accommodating member 2 hits the distal end of the activating element 7. The drive member 3 can then be moved in the proximal direction with respect to the housing 1 over a third insertion distance. While the accommodating member 2 is advanced further with respect to the housing 1 to deflect the holding element 6, the stoppers 4b and 4d are simultaneously also shifted further in the distal direction of the product reservoir 4. Superfluous air can therefore escape from the product chamber 4a through the injection needle 13. It would, in principle, also be conceivable to complete the venting procedure while the first insertion distance is being traveled, and to release the holding position of the holding element during the second and third insertion distances.

FIG. 4A shows an administering device in accordance with the present invention, in an inserted position in which the accommodating member, having traveled the third insertion distance, is completely—e.g. as far as required—inserted into the housing in the proximal direction. Once this third insertion distance has been overcome, the drive member 3 is no longer held by the holding element 6 with respect to the housing. Due to the abutment between the proximal end of the accommodating member 2 and the distal end of the activating element 7, the drive member 3 is slaved over the third insertion distance relative to the housing in the proximal direction, wherein the drive button 8 is moved out of the proximal end of the housing 1 and is then accessible for a user. During the relative movement of the drive member 3 and, therefore, the activating element 7 with respect to the housing 1, the activating element 7 slides along the edge of the protrusion 11, which protrudes inwardly, and is thus deflected inwardly. The third insertion distance, which corresponds to the stroke of the drive member 3 out of the housing, also corresponds to the required advancing distance when advancing the drive member in the distal direction to deliver the product. The third insertion distance thus corresponds to a dosing stroke for the administering device. The insertion distance can therefore be varied in the design of the administering device, in accordance with the required dosing stroke.

FIG. 4B shows a detailed view analogous to FIG. 1B, in which the administering device is situated in an inserted position. When the drive member 3 is moved or raised out of the housing 1, the clamp fitting between the securing element 10 and the protrusion 11 is also overcome.

The accommodating member 2 has then been completely screwed into the housing 1, the active agent has been mixed, and the product chamber has been vented. The administering device has been placed in an activated state with the drive button extended. It is then ready to administer the desired dosage of the active agent.

To this end, the drive member 3 is slid into the housing 1 in the distal direction, as shown in FIG. 5A, wherein the accommodating member 2 remains at rest with respect to the housing 1. This advancing movement is therefore transferred onto the stoppers 4b and 4d, such that the fluid product is delivered or forced from the product chamber 4a. The drive member 3 is advanced in the housing until the drive button 8 abuts against the housing protrusion 9, wherein the activating element 7—which has been deflected inwardly by the protrusion 11—slides on the inner side of the accommodating member 2, into the accommodating member 2. The holding member 6 likewise slides along the inner area of the accommodating member 2, wherein the heel 6a is guided along the circumferential area of the accommodating member 2. As soon as the drive button 8 abuts against the housing protrusion 9, the proximal end of the holding member 6 has also been moved past the housing protrusion 9. A cavity is provided in the inner circumferential area of the accommodating member 2 at the level of the heel 6a, into which the heel 6a can yield. Due to being biased, the holding element 6 springs into the cavity and back into the holding position in which the distal end of the holding element 6 abuts against the housing protrusion 9. The drive button 8 is again countersunk within the housing 1.

The administering device is then situated in an end position, wherein the holding element 6 is again in a holding position, such that the drive member 3 is fixed with respect to the housing 1. The administering device is therefore locked or blocked against being operated any more. FIG. 5B shows the detail from FIG. 1B, with the administering device in an end position. It can be seen that the securing element 10 has again entered into a clamp fitting with the protrusion 11 of the housing 1. This secures the drive member 3 against further movements or wobbling, in addition to the holding engagement between the holding element 6 and the housing protrusion 9. In this secured state, the administering device can then be disposed of.

In some preferred embodiments, it is sufficient for the purpose of the present invention to secure the drive member 3 against moving proximally relative to the housing the holding element 6, i.e., the securing element 10 serves for more comfortable operating and as an additional guide for the drive member 3.

Figure 6A:
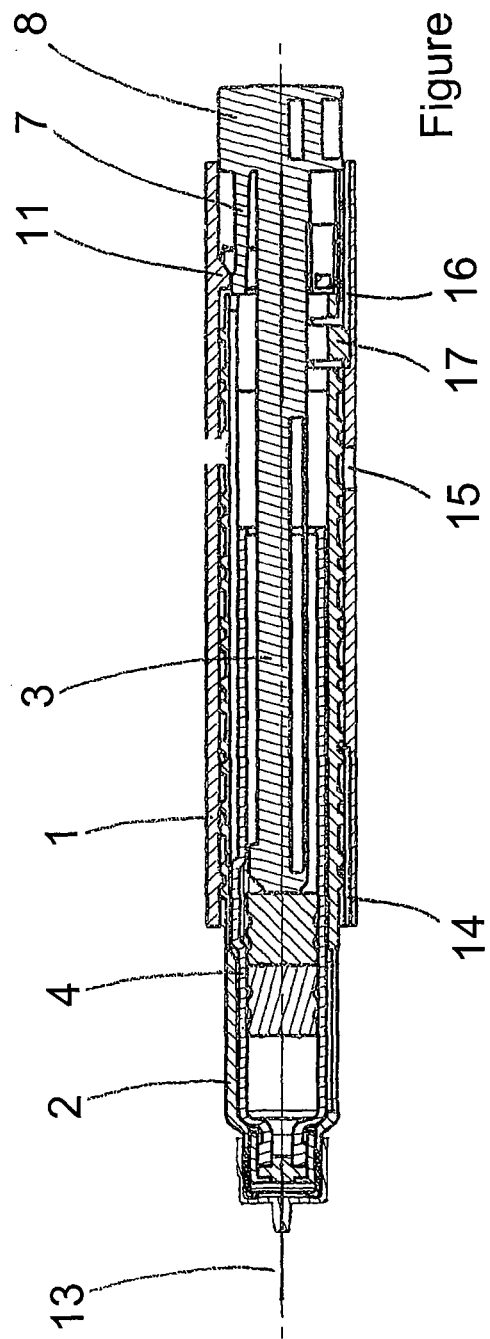
FIG. 6A is a sectional view through an embodiment of an administering device in accordance with the present invention, comprising a latching means.

FIG. 6A shows a section through an embodiment of an administering device in accordance with the present invention from which the latch or latching means and/or indicator or indicating means for latching and/or indicating the individual preparation steps of the administering device is shown. The administering device in FIG. 6A is already in a mixing position. The indicating and/or latching means comprises a first latching flute 14, a second latching flute 15 which can also be formed as a latching opening, and a third latching flute 16. A latching arm 17 which is aligned in the circumferential direction is provided on the accommodating member 2 and biased radially outwardly such that it slides along the inner circumferential area of the housing when the accommodating member 2 is rotated into the housing 1. When the accommodating member 2 is inserted into the housing 1, the accommodating member 2 is rotated into the housing 1 until the latching arm 17 latches with the first latching flute 14. In this latching, the administering device is situated in the initial position. The latching arm 17 is formed such that it blocks the accommodating member 2 from rotating back out of the housing, due to its bias, by abutting against the first latching flute 14. From the initial state, it is therefore only possible to rotate the accommodating member 2 further into the housing 1 in the proximal direction. It is in principle possible to arrange the first latching flute over the length of the housing, such that latching is initiated after each revolution of the accommodating member. The latching between the latching arm 17 and the latching flute generates an indication that the initial state has been reached. From the initial state, the accommodating member is inserted further until it latches with the latching arm 17 in the second latching opening 15, which indicates the completion of mixing in the two-chamber reservoir. If said second latching flute is formed as an opening, it is in principle possible for the latching arm 17 to be pressed in from without, out of the latching opening into the interior, which could also rotate the accommodating member back out of the housing 1. This option would seem expedient in principle if the product is not intended to be administered from the administering device immediately after being mixed. In some embodiments, however, the second latching flute is not formed as an opening, such that this second latching also represents a reverse rotational block for the accommodating member out of the housing. From this mixing position, the accommodating member can be screwed further into the housing in the proximal direction until the latching arm 17 is latched in the third latching flute, which indicates the venting position. The latching between the latching arm 17 and the third latching flute 16 likewise forms a reverse rotational block, such that in this position, the accommodating member is locked against any further movement with respect to the housing, since the accommodating sleeve 2 simultaneously abuts against the housing protrusion 9 in the axial direction.

Figure 6B:
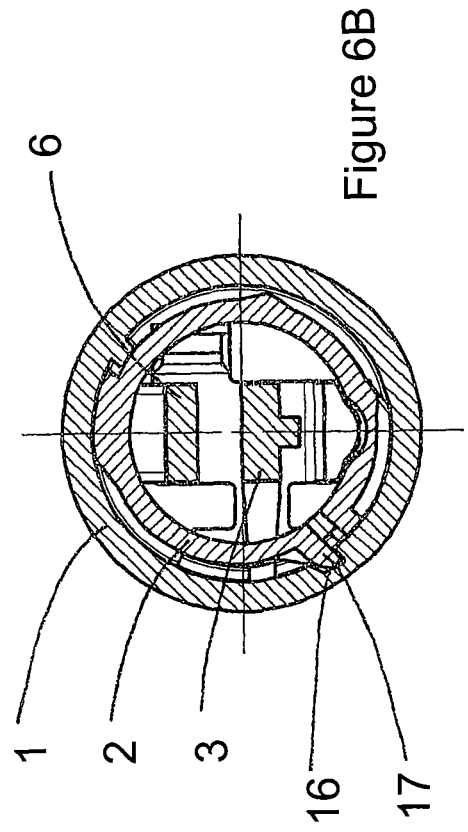
FIG. 6B depicts the administering device according to FIG. 6A, in a venting position.

FIG. 6B shows a cross-section through an administering device, which shows the latching arm 17 and the accommodating member 2 in a latching position with a latching flute in the housing 1. It can be seen from FIG. 6B that the accommodating member 2 is prevented from being rotated anticlockwise by the latch, whereas a clockwise rotation of the accommodating member 2 within the housing 1 is possible by the fact that the latching arm 17 flexibly yields inwardly and can slide out of the flute along the chamfer of the flute.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for administering a fluid product, comprising:
   a) a housing;
   b) an accommodating member for the fluid product and/or for a reservoir for the fluid product, which can be inserted relative to the housing along a longitudinal axis of the housing from an initial position to an inserted position;
   c) a drive member which is mounted in the housing and can be moved relative to the accommodating member to deliver the fluid product from the accommodating member and/or reservoir, wherein
   d) the drive member comprises at least one holding element which holds the drive member relative to the housing in the initial position of the accommodating member and is moveable from the holding position to a released position in which the drive member can be moved relative to the housing by inserting the accommodating member, the drive member further comprising an activating element with which the accommodating member engages during the insertion movement and which moves the drive member relative to the housing to an activated position in which drive member protrudes proximally out of the housing, wherein the activating element abuts an axial abutment on the accommodating member during the insertion movement, lies within the accommodating member in an end position after the fluid product has been administered, and wherein in the end position the holding element abuts the abutment, which is fixed with respect to the housing, and lies substantially within the accommodating member.

2. The administering device according to claim 1, wherein the holding element comprises a heel which limits a movement of the drive member in the proximal direction relative to the housing by abutting an edge which is fixed with respect to the housing.

3. The administering device according to claim 2, wherein the accommodating member is formed in the shape of a sleeve and comprises a cavity with which the heel of the holding element engages in the end position.

* * * * *

UNITED STATES PATENT AND TRADEMARK OFFICE
CERTIFICATE OF CORRECTION

PATENT NO. : 8,216,180 B2  
APPLICATION NO. : 12/572759  
DATED : July 10, 2012  
INVENTOR(S) : Tschirren et al.

Page 1 of 1

It is certified that error appears in the above-identified patent and that said Letters Patent is hereby corrected as shown below:

SPECIFICATION

| Column | Line | PTO | Should Read |
|---|---|---|---|
| 13 | 18 | "the housing the holding" | -- the housing using the holding -- |

Signed and Sealed this  
Twenty-third Day of October, 2012

David J. Kappos  
*Director of the United States Patent and Trademark Office*